United States Patent [19]
Nagel

[11] Patent Number: 5,582,195
[45] Date of Patent: Dec. 10, 1996

[54] DEVICE FOR DISPENSING BOTH DENTAL FLOSS AND MOUTHWASH

[76] Inventor: Richard R. Nagel, 15750 Vista Ave., Lombard, Ill. 60148

[21] Appl. No.: 329,265

[22] Filed: Oct. 26, 1994

Related U.S. Application Data

[63] Continuation-in-part of Ser. No. 114,214, Aug. 30, 1993, abandoned.

[51] Int. Cl.$^6$ .................................................... A61C 15/04
[52] U.S. Cl. ......................................................... 132/324
[58] Field of Search ..................................... 132/321, 323, 132/324, 325, 328

[56] References Cited

U.S. PATENT DOCUMENTS

| | | | |
|---|---|---|---|
| 2,128,701 | 8/1938 | Gelinsky | 606/228 |
| 3,830,247 | 8/1974 | Kaphalakos | 132/325 |
| 3,902,510 | 9/1975 | Roth | 132/222 |
| 4,019,522 | 4/1977 | Elbreder | 132/325 |
| 4,231,381 | 11/1980 | Battista | 132/322 |
| 5,065,861 | 11/1991 | Greene et al. | 206/63.5 |
| 5,076,302 | 12/1991 | Chari | 132/324 |

*Primary Examiner*—Todd E. Manahan

[57] ABSTRACT

A closure which allows the dispensing of mouthwash and the dispensing of dental floss from a single container. The closure has apertures through it and a tube reaching very close to the bottom of the container. This tube suspends a roll of dental floss, which is attached to the tube, into the liquid mouthwash inside the container. Apertures in the closure allow a user to dispense some of the contents of the container for rinsing purposes by merely tipping the container as a user would tip a container of ordinary mouthwash. The loose end of the submerged and saturated dental floss attached to the tube of the closure is threaded upward through the bottom of the tube where it can be grasped by the user, pulled to a desired length, cut off by a cut off device and then used to floss the teeth. The cut off end of the floss remains at the cut off device, ready to grasp for the next usage.

5 Claims, 11 Drawing Sheets

DEVICE FOR DISPENSING BOTH DENTAL FLOSS AND MOUTHWASH

This application is a continuation-in-part of Ser. No. 08/114,214 filed Aug. 30, 1993, now abandoned.

TECHNICAL FIELD

This invention relates to product dispensing closures and containers and in particular to the dispensing of wet dental floss and liquid mouth wash from the same container.

BACKGROUND OF INVENTION

Proper care of teeth and gums reduces the incidence of periodontal disease and dental cavities, thereby reducing the loss of teeth. Good personal dental hygiene consists of regular brushing, regular flossing, regular use of plaque loosening rinses and, in some instances, fluoride rinses. Most people brush their teeth, fewer people use regular mouth washes, fewer still use plaque loosening or fluoride coating rinses, and it is estimated that less than 10% of the American public regularly floss their teeth.

DESCRIPTION OF PRIOR ART

Although regular brushing is helpful in reducing cavities, brushing alone does not reach completely between two abutting or touching teeth and therefore does not brush away food particles or plaque at the these locations. Use of a mouth wash may rinse away some particles of food from between the teeth if the teeth do not touch. Rinses of plaque softener will soften plaque between teeth but will not rinse it away, nor will it penetrate between the surfaces of teeth that are in actual contact with each other. Therefore a plaque softener cannot soften plaque which has accumulated upon the touching surfaces. The same lack of penetration applies to the use of fluoride rinses. Of currently known techniques, only flossing can safely penetrate between the touching surfaces of abutting teeth, remove food particles and coat teeth with plaque softener or fluoride at those locations. Hence the need for a method of wetting dental floss with a given therapeutic liquid. This need for dispensing wet floss is evidenced by the issue of numerous patents in the field, among them, U.S. Pat. Nos. 3,830,247; 3,902,510; 4,109,522; 5,065,861; 5,076,302 and 4,231,381. All of these ideas are workable but all are a single use: the wetting and dispensing of floss. In addition, all are expensive to tool up for, to manufacture and none of them provide any incentive for their use by being more convenient, less expensive or taking up less shelf space in a medicine cabinet.

Although much of the prior art can effectively aid in preventing cavities by introducing wet floss as well as by rinsing, no single piece of prior art can accomplish both of these requirements. To accomplish what this invention proposes by means of existing prior art will require the purchase of two items, their separate storage and their separate costs.

A need exists for a means of introducing wet floss to the surfaces of touching teeth as well as dispensing liquid from the same container. This means should be easy to use, should automatically remind the user to both floss and rinse and should be economical to produce. This means should require little further user education, should be compatible with current advertising and distribution channels of the producer, should take up little or no additional shelf space in the home or on the store shelves. It should also cost the consumer less than the separate purchase of floss and liquid preparations when purchased as separate items. A means which has these characteristics will provide improved dental health to the public at reduced cost.

SUMMARY OF THE INVENTION

The invention is a closure for a container which includes a spool of dental floss submerged in the contents of the container. Means are provided for dispensing wet floss from the container, cutting the floss and pouring out a portion of the contents of the container for use as a mouth wash or rinse. Of importance and a unique feature of this invention is that the floss dispensed will always be wet without having to shake the container or turn it upside down. Of equal importance is that both wet floss and liquid for an oral rinse will be dispensed from a single container.

There are several preferred embodiments to this invention. In all of the embodiments a roll of dental floss is placed around a hollow tube. The floss is threaded from the roll up through the bottom of the tube, out the top of the tube and through an aperture in the closure. The closure, with tube and floss, is then inserted into the container and the container is sealed shut. One embodiment of the closure is a flip top cap. The flip top cap can have several variations in design. A first variation would permit the dispensing of floss only, a second variation would permit dispensing of a measured amount of liquid as well as dispensing floss and a third variation would allow dispensing an unmeasured amount of liquid to as well as floss. The cap not only carries the floss and liquid dispensing mechanisms but also is the means of sealing the container. Another embodiment of the closure is a cork which is inserted into the neck of a container. This variation would require a separate cap to seal the container. The cork, itself, can have several variations in design, a first variation would permit dispensing floss only, a second variation would permit dispensing of a measured amount of liquid and a third variation would permit both an unmeasured amount of liquid and floss to be dispensed.

COMBINATION AND MODIFICATION OF PRIOR ART TECHNIQUES, PRODUCTS AND DEVICES INTO A NEW CONCEPT TO IMPROVE THE PREVENTION OF CAVITIES

Combining and modifying features of present practice into this new concept can aid materially in the prevention of cavities in a more convenient and a more economical manner than is now possible. This invention will provide a combination of a liquid wash, medication or plaque softener with the use of dental floss impregnated with a medication or mouthwash to be dispensed from the same container. This concept will permit the treatment of abutting and touching tooth surfaces with a medicated substance as well as rinse the teeth with a wash without the inconvenience of using two separate containers, storing two separate containers or purchasing two separate containers. The use of this invention will encourage more people to both floss their teeth and to rinse their teeth hence promoting dental health at reduced cost and added convenience.

OBJECTS AND ADVANTAGES

Several objects and advantages of this invention are:

a. To prevent cavities.

b. To make it more convenient to prevent cavities than is now possible.

c. To do (a) and (b), above, less expensively than is now possible.

d. To provide a single container with closure which will serve the dual purpose of dispensing liquid and to dispense wet dental floss.

e. To provide a container with closure which can dispense liquid by pouring.

f. To provide a container with closure which can dispense measured amounts of liquid.

g. To provide a container with closure which dispenses wet floss only, not liquid.

h. To provide a container with closure having a cutting device as an integral part of the container with closure.

i. To provide a container with closure which dispenses wet floss even when the liquid level is at or near the bottom of the container without shaking or turning the container over.

NUMERICAL LISTING OF PART NUMBERS

Figure 1:
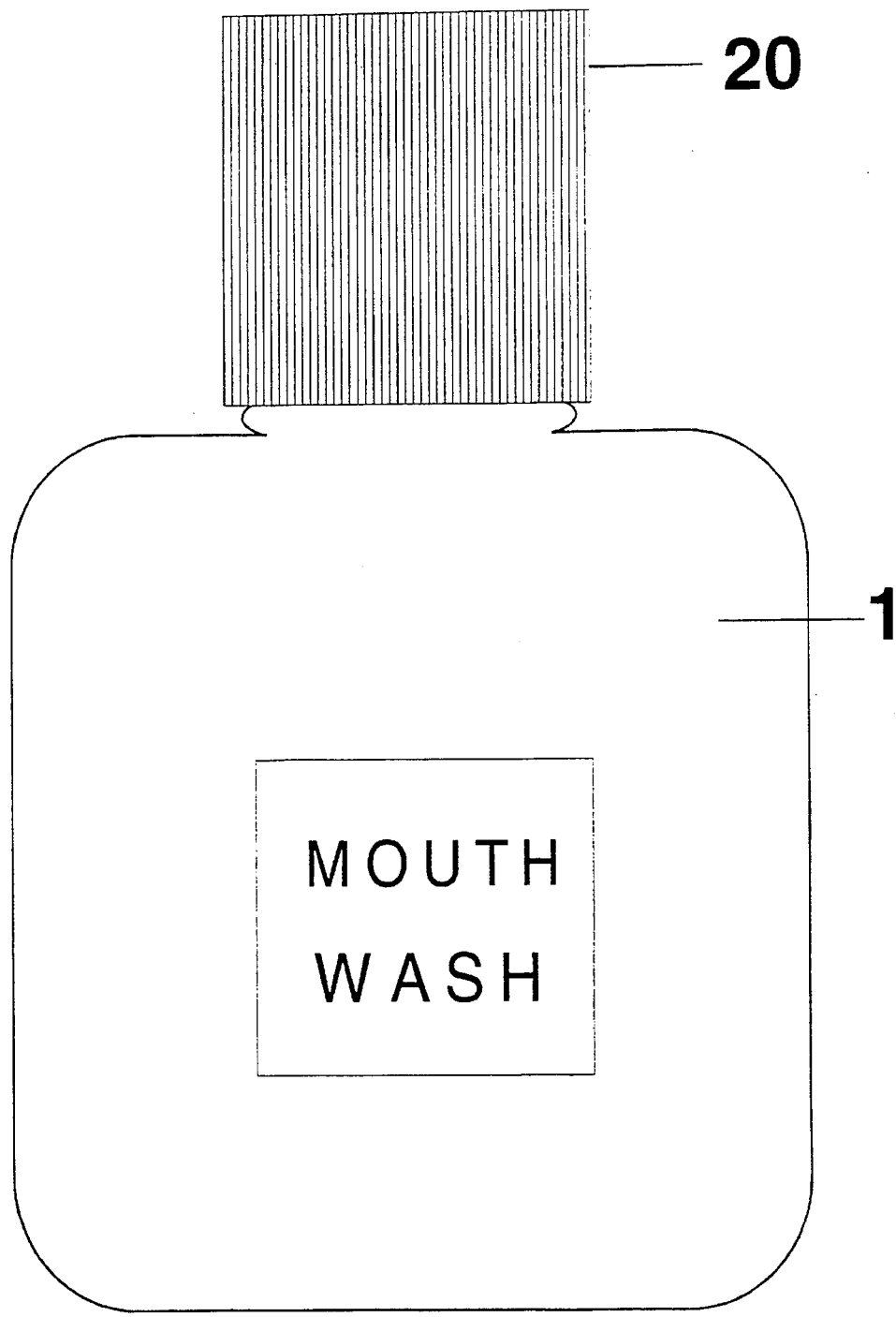
FIG. 1 is a front view of the outward appearance of a generic container and closure cap.

1 Container, Generic
2 Container, Utilizing Both Cork and Cap
2A Container (2), Neck
2B Container (2), Neck Extension
3 Container, Utilizing Combination Cap/Cork
3A Container (3), Neck
10 Cork, Unmeasured Liquid and Floss
11 Cork, Measured Liquid and Floss
12 Cork, Floss Only
20 Cap, Generic
21 Cap, For Corked Container
22 Cap, Floss Dispensing Only
22A Cap (22), Floor
22B Cap (22), Flip Top
23 Cap, Liquid and Floss Dispensing
23A Cap (23), Floor
23B Cap (23), Flip Top
23C Cap (23), Channels Therethrough
24 Cap, Measured liquid and floss dispensing
24A Cap (24), floor
24B Cap (24), flip top
24C Cap (24), aperture
30 Tube
40 Floss, Roll
41 Floss, String
42 Floss, Guide
50 Cut Off Device
60 Plugs
80 Spool or Mandrel
90 Liquid Contents of Containers
91 Liquid Contents of Container, Measured

LIST OF REFERENCE NUMERALS

Figure 2:
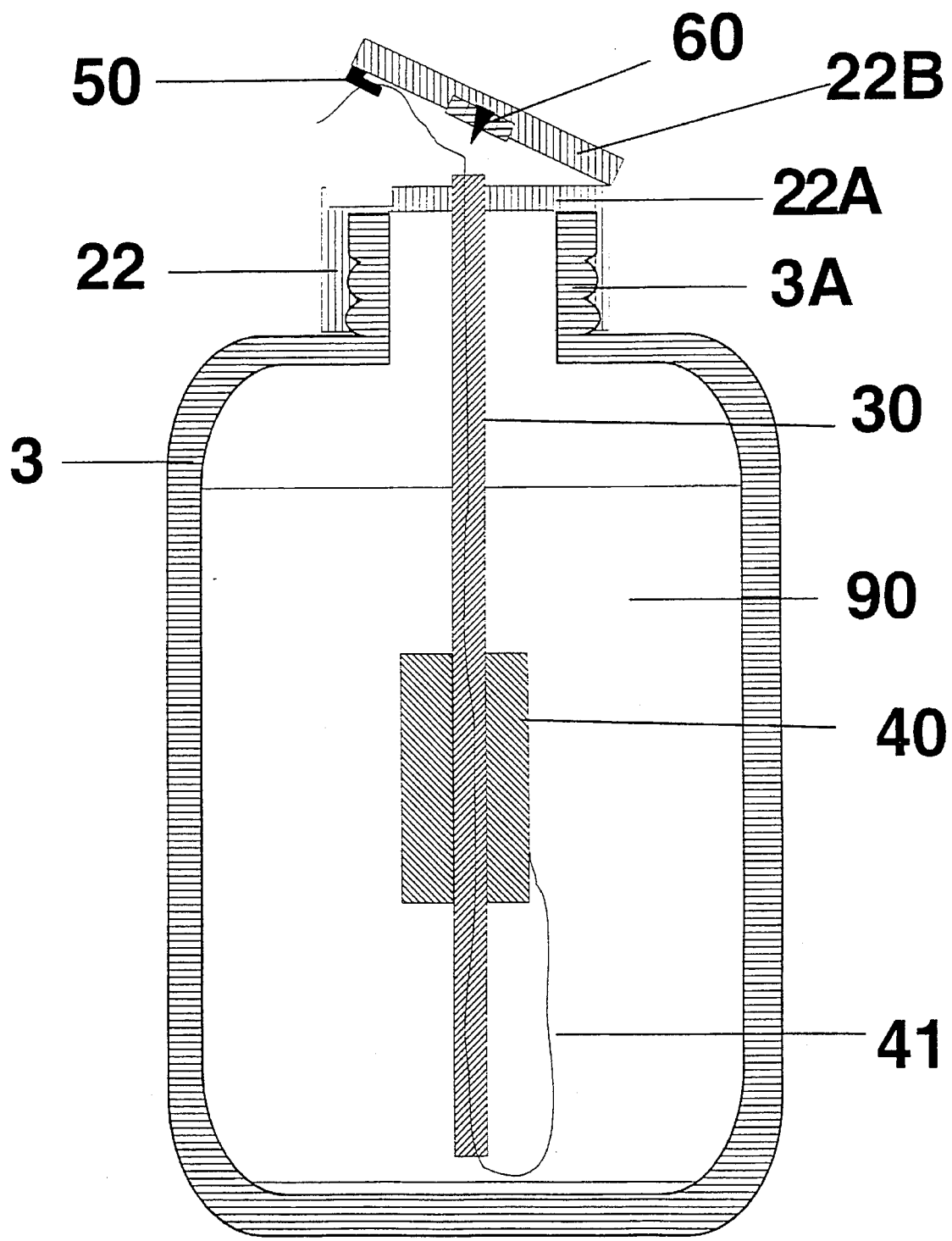
FIG. 2 is a cross sectional view of a container for dispensing wet floss only, having a flip top cap as an integral part of the floss dispensing mechanism.
Figure 3:
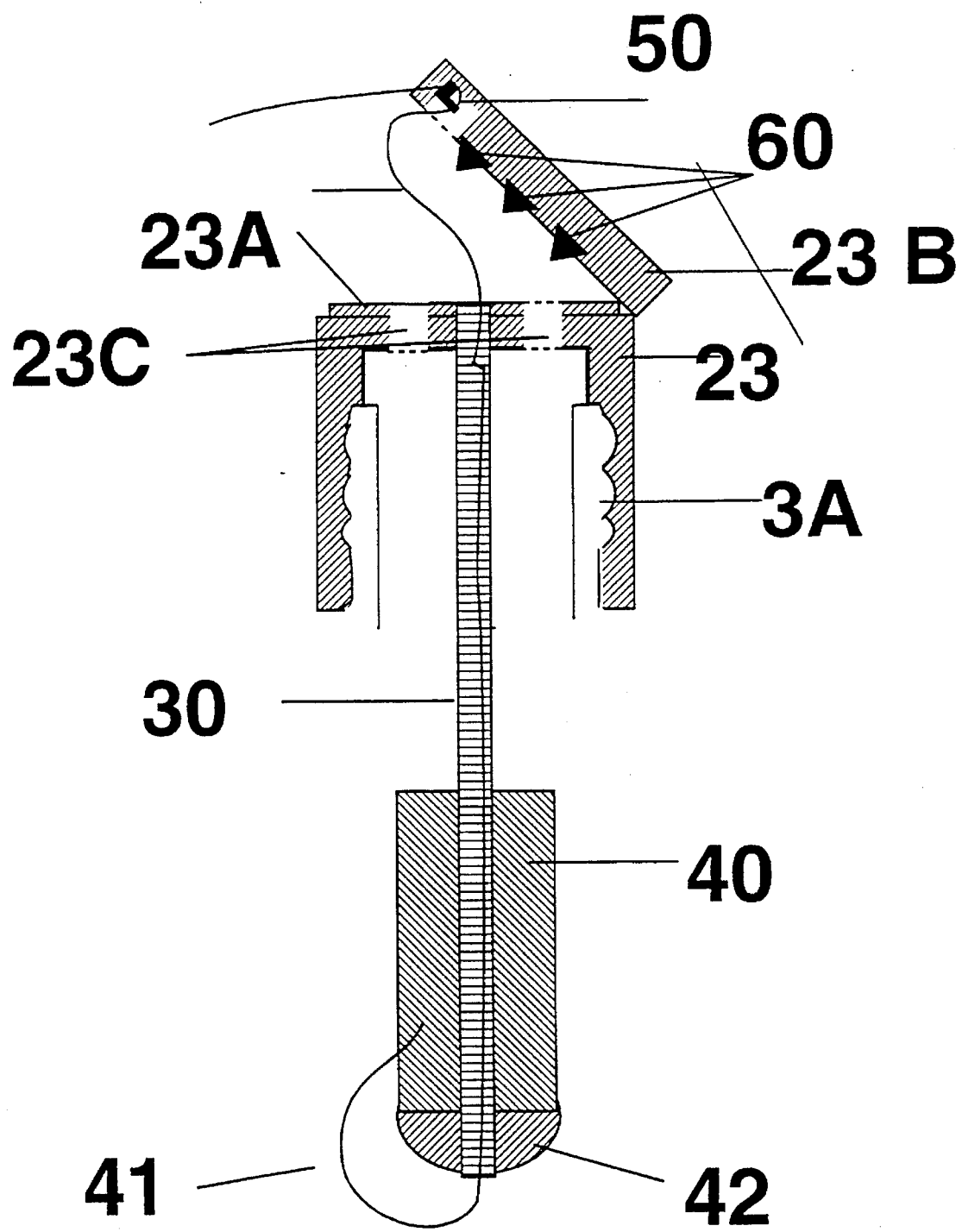
FIG. 3 is a cross section view of a wet floss dispensing mechanism having a flip top cap as an integral part thereof which allows for the pouring of an unmeasured amount of liquid through the cap when the lid is flipped open.
Figure 4:
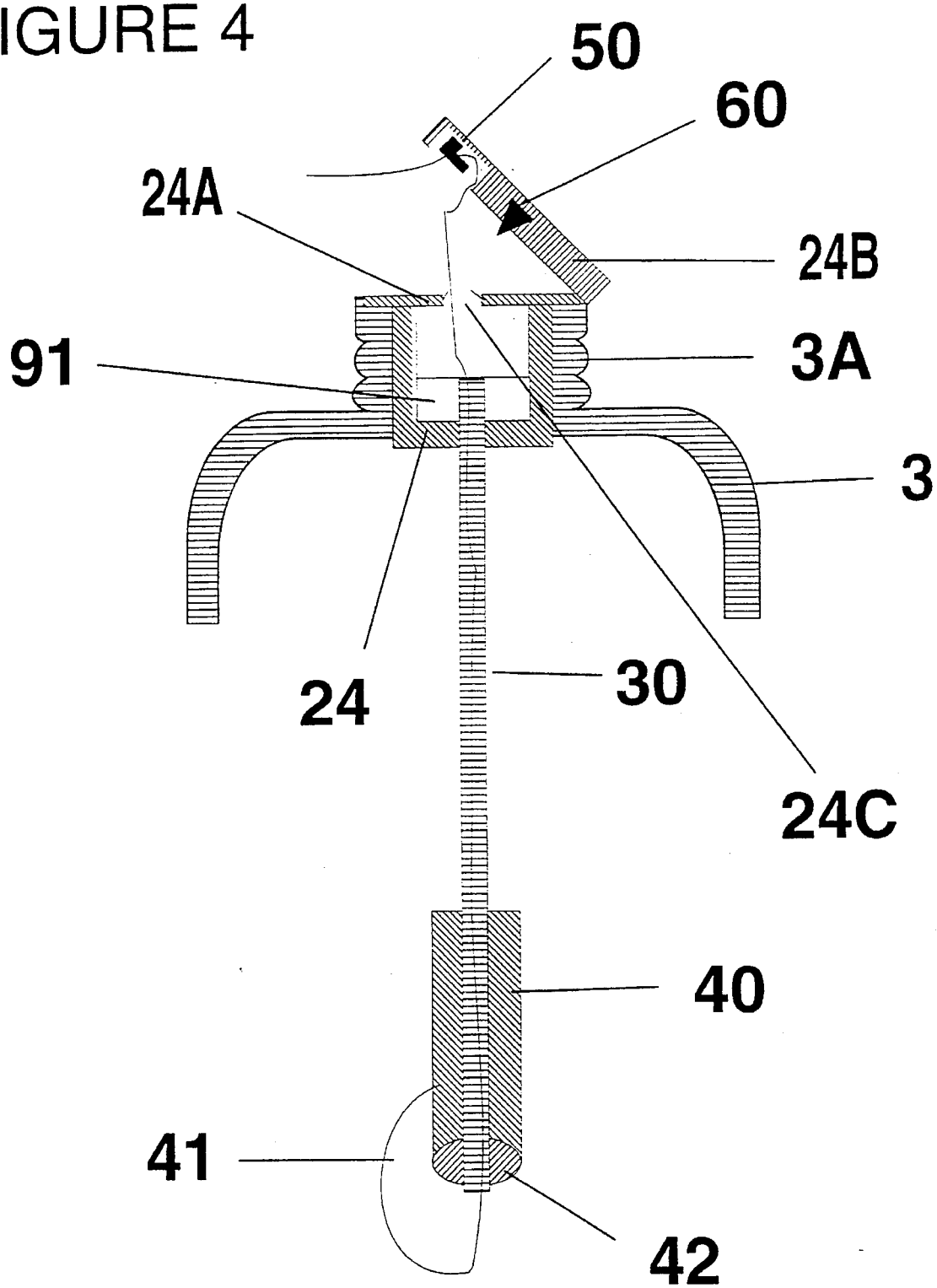
FIG. 4 is a cross section view of a floss dispensing mechanism inserted into the neck of a container, said mechanism configured to allow both dispensing of wet floss and a measured amount of liquid.
Figure 5:
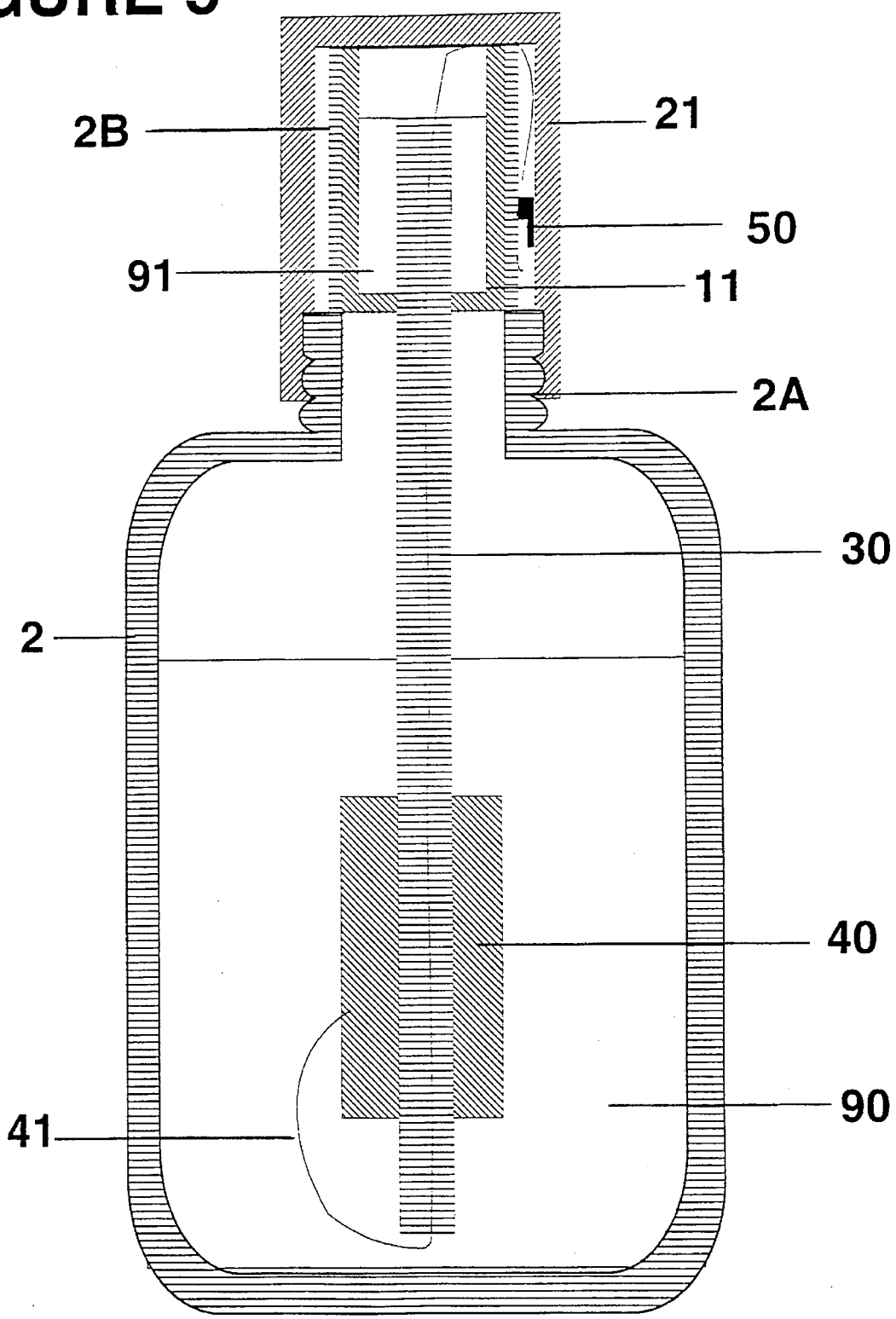
FIG. 5 is a cross section view of a floss dispensing device, inserted into a container having a separate closure cap and a floss cutting device attached to the neck of said container.
Figure 6:
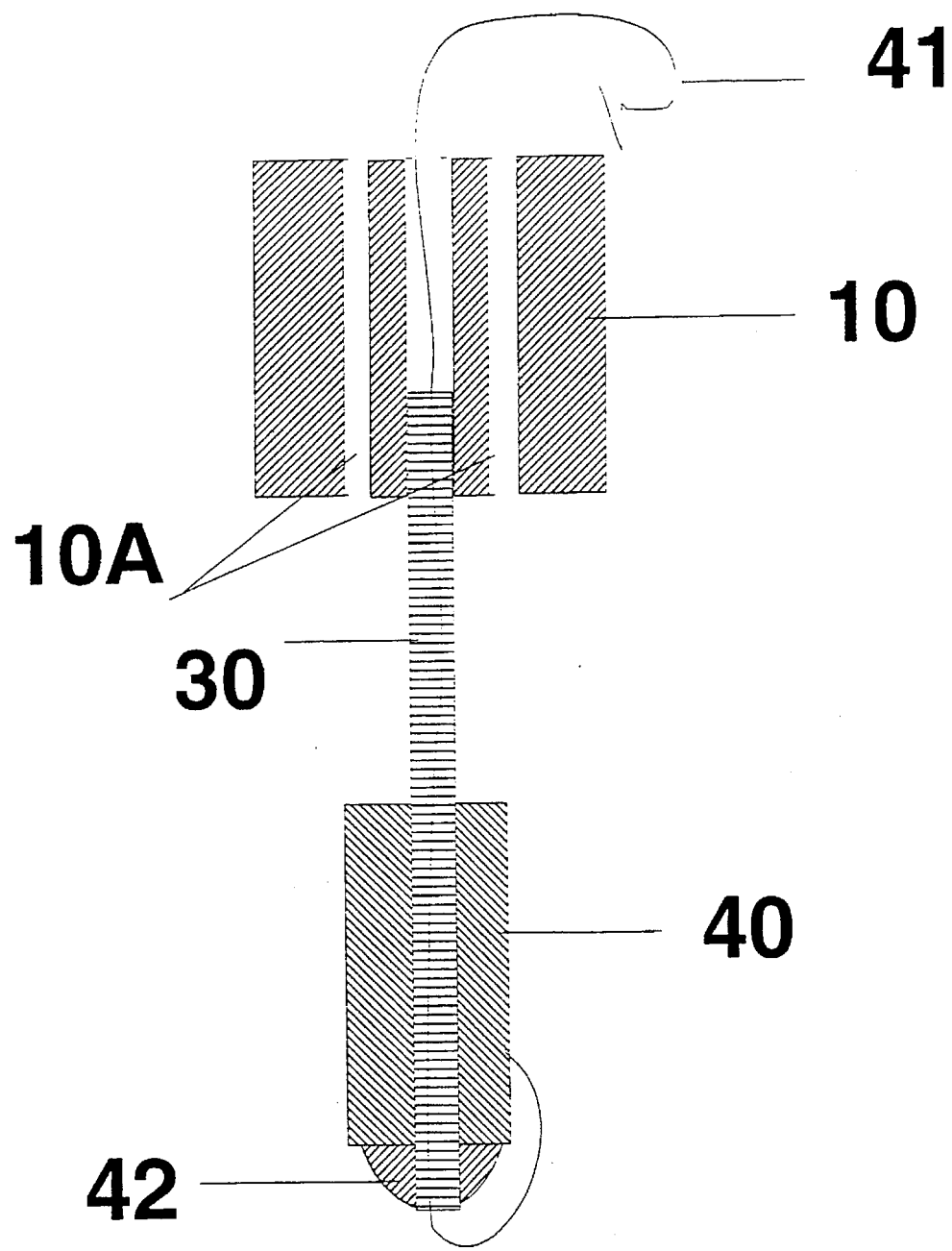
FIG. 6 is a cross section of a floss dispensing device without an integral cap, which device allows dispensing wet floss and an unmeasured amount of liquid.
Figure 7:
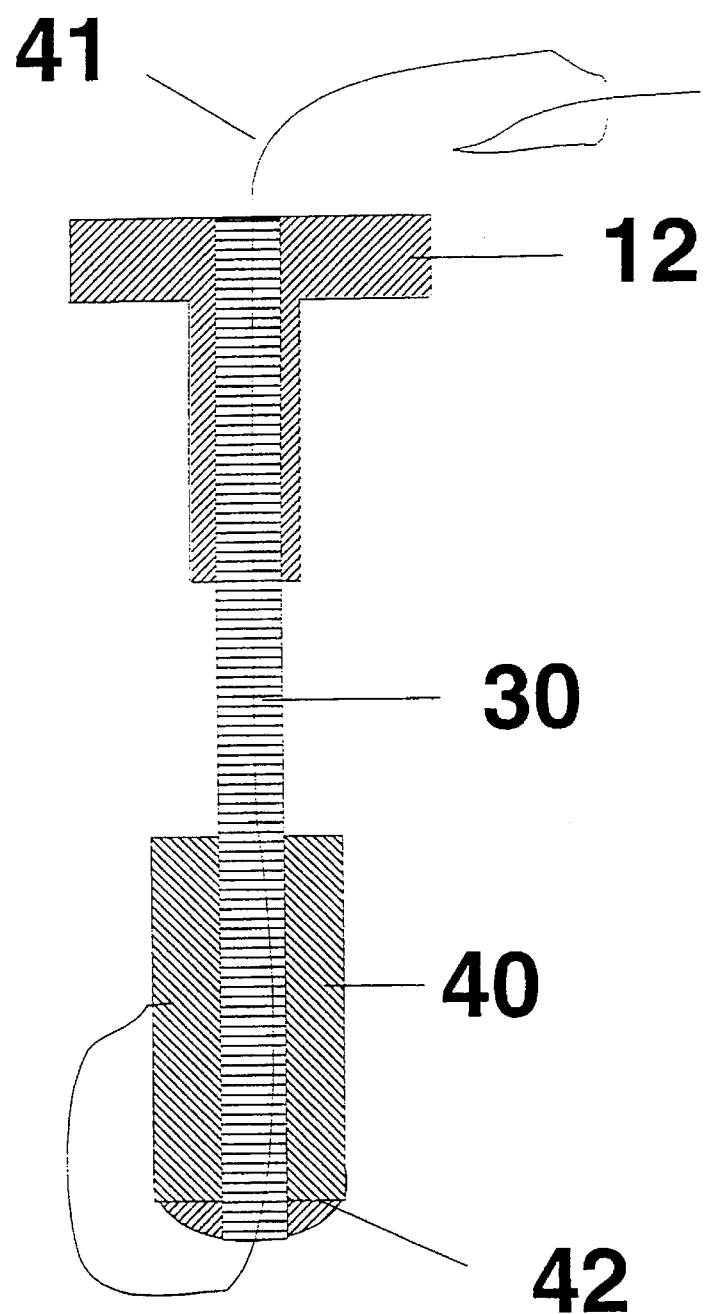
FIG. 7 is a cross sectional view of a floss dispensing device without an integral cap and suitable for dispensing floss only.
Figure 8:
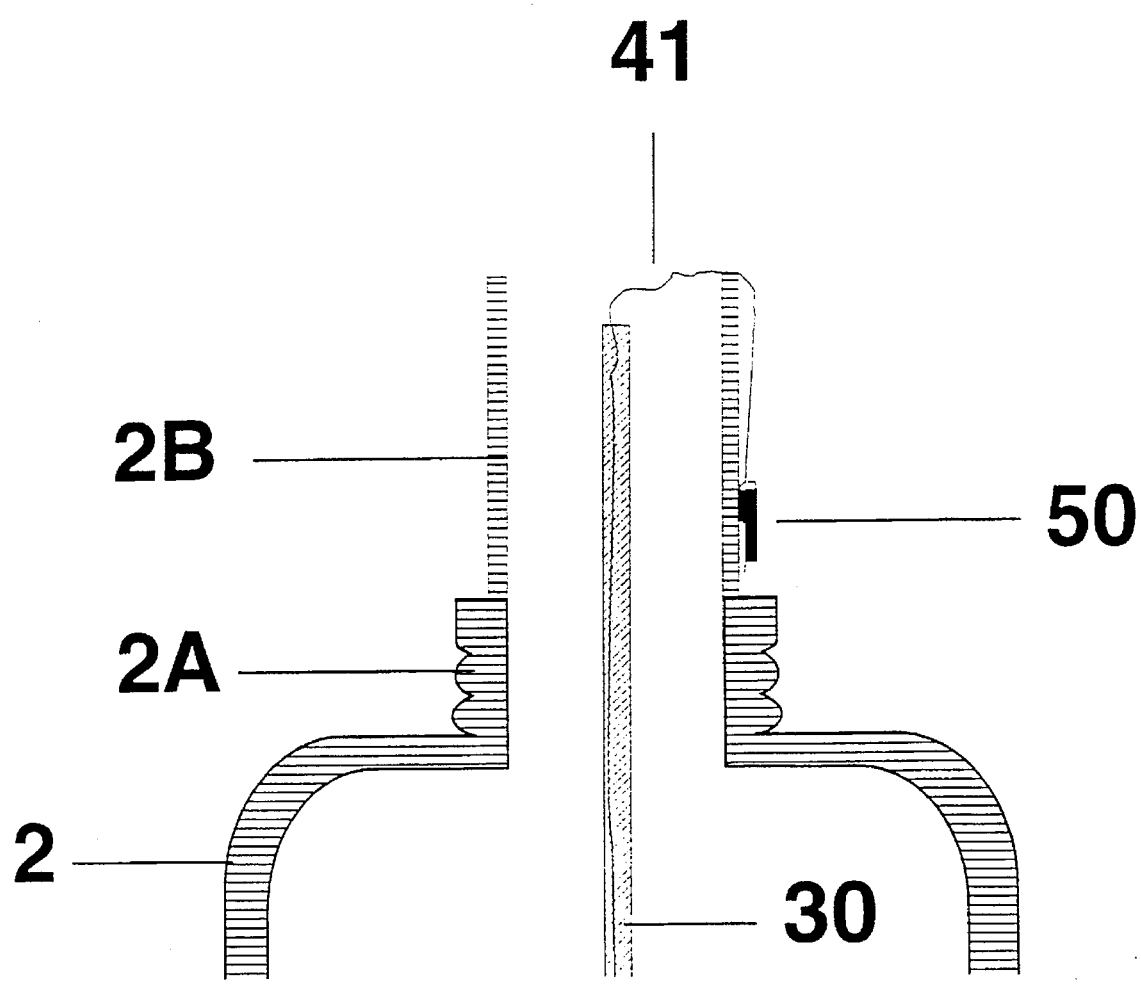
FIG. 8 is a cross sectional view of a container where a floss cutting device is attached to the neck of the container.
Figure 9:
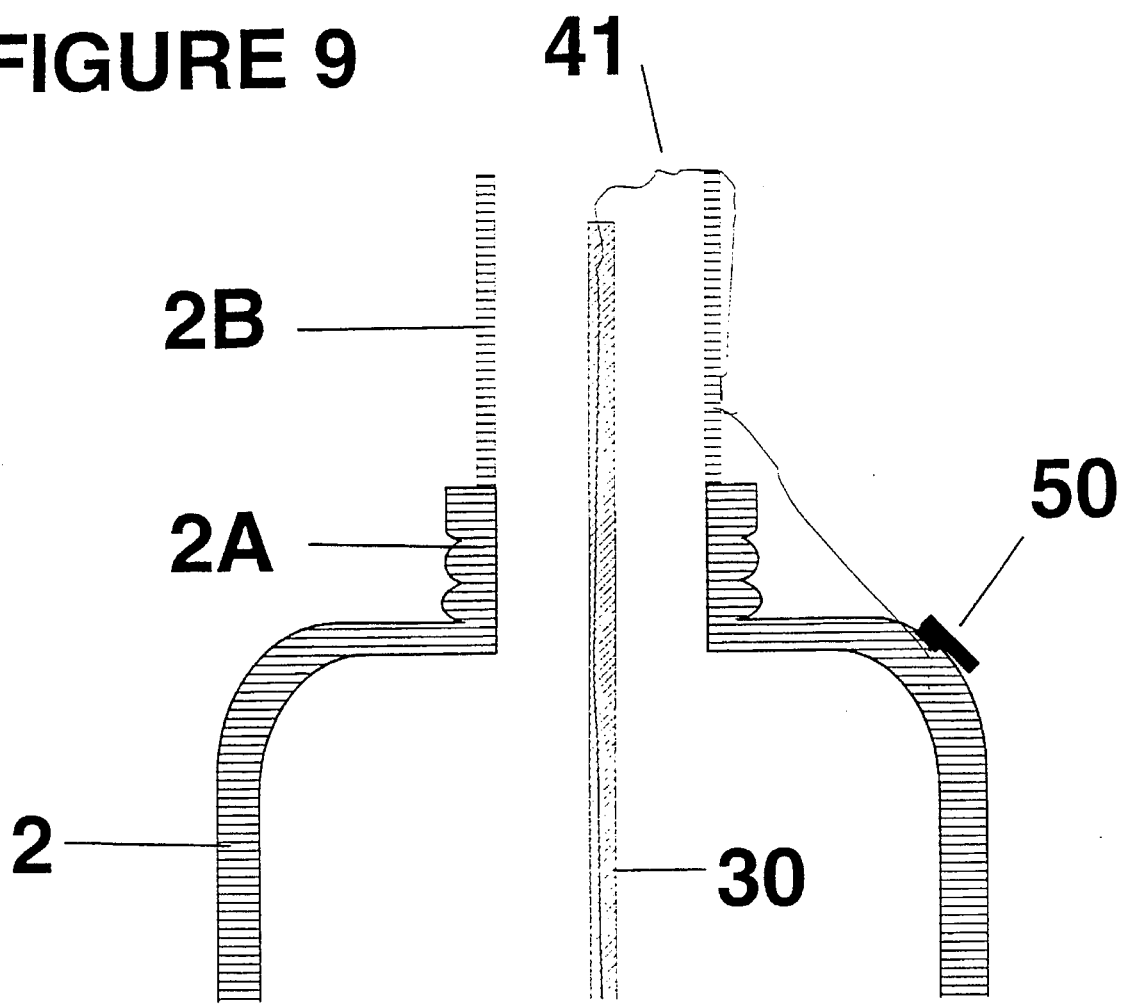
FIG. 9 is a cross section view of a container where a floss cutting device is attached to the body of said container.
Figure 10:
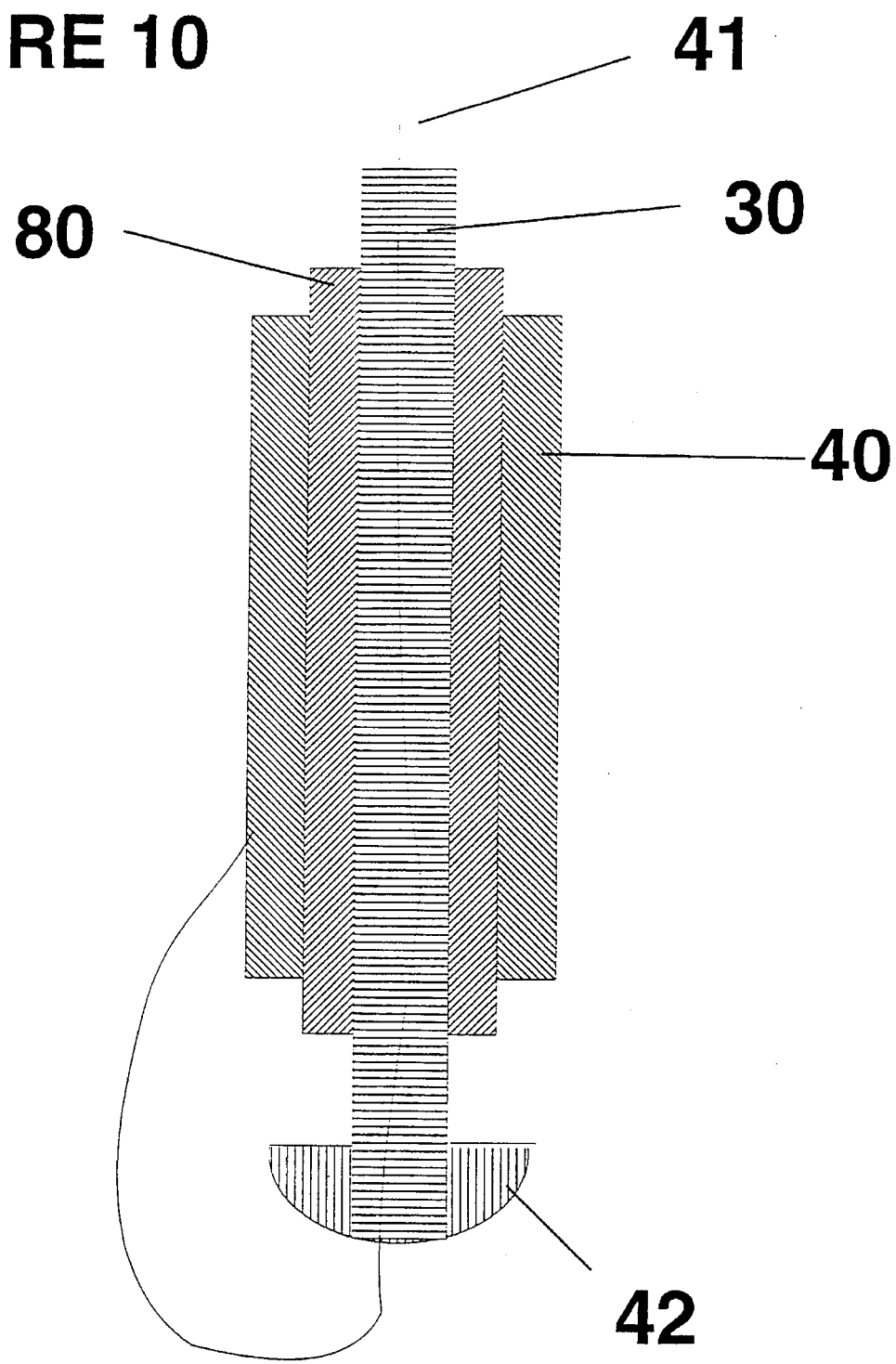
FIG. 10 is a cross sectional view of a roll of floss wound on a mandrel, said mandrel then mounted on the tube portion of a floss dispensing device.
Figure 11:
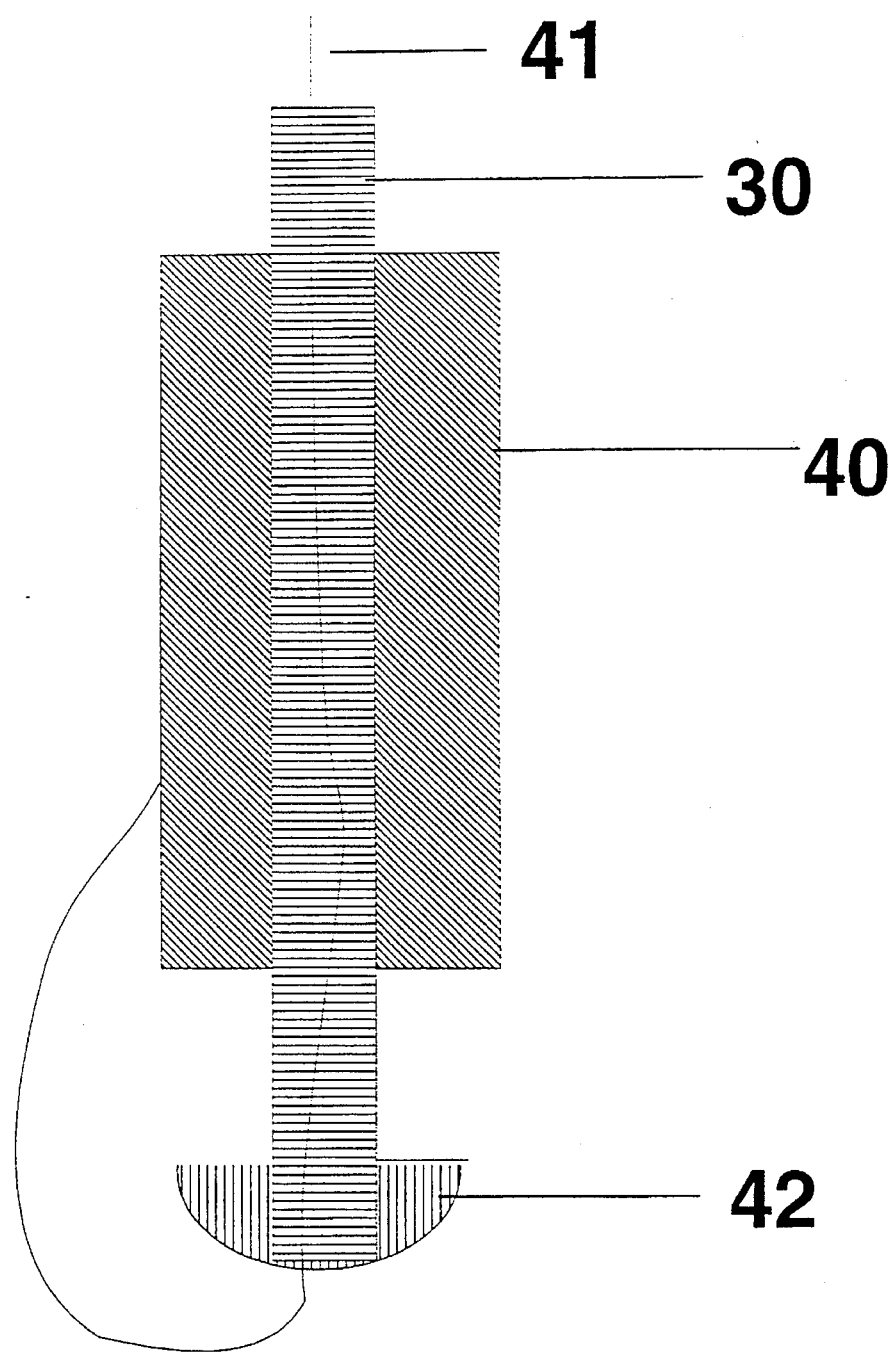
FIG. 11 is a cross sectional view of a roll of floss wound directly onto the tube of a floss dis pensing device.

FIG. 1-Generic Container and Cap
1 Container, generic
20 Cap, Generic
FIG. 2-Container-Flip Top Cap-Floss Dispensing Only
3 Container
3A A Container (3) neck
22 Cap, floss dispensing only
22A Cap (22) floor
22B Cap (22) flip top
30 Tube
40 Floss, roll
41 Floss, string
50 Cut off device
60 Plug
90 Liquid contents of container (2)
FIG. 3-Cap, Flip Top-Unmeasured Liquid and Floss Dispensing
3A Container (3) neck
23 Cap, unmeasured liquid and floss dispensing
23A Cap (23), floor
23B Cap (23) flip top
23C Cap (23), channels therethrough
30 Tube
40 Floss, roll
41 Floss, string
42 Floss, guide
50 Cut off device
60 Plugs, channels and floss aperture
FIG. 4-Cap, Flip Top-Measured Liquid and Floss Dispensing
3 Container
3A Container, short neck
24 Cap, Flip Top-Measured Liquid and Floss Dispensing
24A Cap (24) floor 24B Cap, Flip top
24C Cap, aperture
30 Tube
40 Floss, roll
41 Floss, string
42 Floss, guide
50 Cut off device
60 Plug
91 Liquid, measured amount
FIG. 5-Long Neck Container-Measured Liquid and Floss dispensing
2 Container
2A Container (2) neck
2B Container (2) neck extension
11 Cork, measured liquid and floss
21 Cap, corked container
30 Tube
40 Floss, roll
41 Floss, string
50 Cut off device
90 Liquid contents of container
91 Measured liquid contents
FIG. 6-Cork, Unmeasured Liquid and Floss Dispensing
10 Cork, unmeasured liquid and floss
10A Cork, channels therethrough
30 Tube
40 Floss, roll
41 Floss, string
42 Floss, guide
FIG. 7-Cork, Floss Dispensing Only
12 Cork, floss
30 Tube
40 Floss, roll
41 Floss, String
42 Floss, guide
FIG. 8-Position of Cut Off Device on Neck of Container
2 Container
2A Container, neck
2B Container, neck extension
30 Tube
41 Floss, string
50 Cut off device
FIG. 9-Position of Cut Off Device on Body of Container
2 Container
2A Container, neck
2B Container, neck extension
30 Tube
41 Floss, string
50 Cut off device
FIG. 10-Floss Roll Wound on Spool or Mandrel
30 Tube
40 Floss, roll
41 Floss, string
42 Floss, guide
80 Spool or Mandrel
FIG. 11-Floss Roll Wound Directly onto Tube
30 Tube 40 Floss, roll
41 Floss, String
42 Floss, guide

DETAILED DESCRIPTION OF THE INVENTION

While this invention is susceptible of embodiment in many ways, there is shown in the drawings and will be described here in detail preferred embodiments with the understanding that the present disclosure is to be considered as an exemplification of the principles of the invention and is not intended to limit the broad aspects of the invention to the embodiments illustrated.

FIG. 1 shows what the general outward appearance of the embodiments would look like. All embodiments could well be similar in outward appearance. The visible parts would be the container itself 1 and a closure cap 20. It is obvious that the outward appearance of this invention is little different than the appearance of any common dental hygiene product such as Scope, PLAX or ACT. The differences of this invention from any previous one will be made clear in the description of each of the embodiments shown.

FIG. 2 is a novel combination of a container 3, holding a liquid 90, a closure cap 22, a roll of dental floss 40, a hollow tube 30 and a cut off device 50. This embodiment is intended for dispensing wet dental floss only. The roll of floss 40 is wound around the tube 30. Tube 30 is connected to the floor 22A of cap 22. The flip top 22B of cap 22 is hinged to the body of cap 22 and in this drawing is shown in open position. A string of floss 41 is pulled from the roll of floss 40, threaded up tube 30 from the bottom until it projects beyond the top of tube 30 and above the top of floor 22A of cap 22. The string of floss 41 is then grasped and pulled out far enough to enable it to be tucked under cut off device 50 which is attached to the underside of the flip top 22B of cap 22. The assembly of cap 22, tube 30 and roll of floss 40 can now be inserted into container 3 which has been previously filled with liquid. Cap 22 can now be screwed onto neck 3A of container 3, and the flip top 22B of cap can be closed, plug 60 being inserted into the end of tube 30, making the container 3 liquid tight. The floor 22A and the flip top 22B of cap 22 should also be configured to fit tightly onto each other to facilitate a tight liquid seal for container 3.

The use of this container/cap assembly would be appropriate for dispensing floss impregnated with medication not suitable for rinsing but suitable for flossing. Such a use might be applicable for use with enamel sealant material. In addition dry powders such as abrasive cleaning agents could also be dispensed from this configuration.

The procedure for use would be to open the flip top 22B of cap 22, grasp the floss string 41, pull out the desired length of floss string 41, cut off string 41 at cut off device 50 and proceed to floss. The cut string 41 will remain at the cut off device 50 until needed for the next flossing.

FIG. 3 shows the embodiment of cap 23 which allows for the dispensing of both floss and an unmeasured amount of liquid from container 3. Channels 23C through the floor of cap 23 allow liquid to be poured from container 3 in any desired amount. Plugs 60 on the underside of the flip top cap portion 23B of cap 23 will plug the channels 23C when the flip top lid 23B is closed. The raised portion 23A of cap 23 will fit into the underside of the flip top cap 23B when said flip top is closed thereby helping to ensure a liquid tight closure.

The procedure for using this embodiment to dispense floss 40 is the same as that described for FIG. 2. To dispense liquid 90 from this embodiment one must merely open the flip top 23B and tip the container 3.

FIG. 4 shows the embodiment of cap 24 which allows the the dispensing of both floss and a measured amount of liquid from container 3. A single channel 24A allows both liquid 91 and floss string 41 to be taken or poured from container 24. A cup like configuration 24A of cap 24 fits into the neck 3A of container 3. The top of tube 30 is positioned in the interior of this cup like configuration 24A. The top of tube 30 is placed at a level which will allow liquid 91 to rise to ithe tube 30 top. Any liquid 91 in excess of this level will flow back down tube 30 into the body of container 3. With cap 24 closed, the cup like portion 24A will be filled by squeezing the flexible body of container 3. This squeezing will force liquid up tube 30 where it will fill the cup like portion 24A of cap 24. Any excess liquid 91 beyond the desired amount, as determined by the placement of the top of tube 30, will flow back down tube 30.

The procedure for using this embodiment to dispense floss 40 is the same as that described for FIG. 2. To dispense liquid 91 from this embodiment one must merely open the flip top 24B and tip the container 3.

FIG. 5 is a novel combination of a container 2, holding a liquid 90 and 91, a roll of dental floss 40, a hollow tube 30, an unchanneled cork 11 having a cup like configuration the sides of which fit snugly into the elongated neck 2B of container 11 and a cut off device 50. This container 2 must be made of a flexible material since it will be necessary to squeeze the container 2 to force liquid 90 up into the cup like cork 11. This embodiment is intended to dispense wet dental floss 41 and a measured amount of liquid 91. The roll of floss 40 is wound around tube 30. The tube 30 is attached to the unchanneled cork 11. The top of tube 30 is positioned at a height inside the cup like cork 11 which will determine how much liquid will be dispensed. A string of floss 41 is pulled from floss roll 40 and threaded through tube 30 from the bottom of tube 30 upward until it protrudes from the top of tube 30. This sub assembly of cork 11, tube 30 and threaded floss 40 will be inserted into the neck 2A of container 2 which has been previously filled with liquid. The string of floss 41 protruding from the top of the inserted cork 11 will be grasped, pulled to a desired length and wrapped under the cut off device 50 which is attached to the exterior of the elongated neck 2B of container 2. A closure cap 21 can now be screwed onto the neck 2A of container 2 and the package is complete.

To use this embodiment the cap 21 must be unscrewed and removed. To floss, the user would grasp floss string 41 located at the cut off device 50, pull a desired length of floss string 41, cut the floss string 41 by pulling it under cut off device 50 and proceed to floss. To pour out a measured amount of liquid the user would squeeze the container 2 while the cap 21 was still secured on neck 2A of container 2. Squeezing the container 2 will force liquid 90 up tube 30 into the cup like cork 11. Liquid 91 will accumulate in the cup like cork 11 until a liquid 91 level is reached at the exact height of the top of tube 30. Any liquid 90 forced up tube 30 in excess of that amount will flow back down tube 30 when squeezing of container 2 is stopped. After filling the cup like cork 11, user will remove cap 21 and pour out the measured amount of liquid 91.

FIG. 6 shows the embodiment of cork 10 which can be used in place of cork 11, FIG. 5 to allow for the dispensing of both floss 40 and an unmeasured amount of liquid 90. Channels 10A through cork 10 allow liquid 90 to be poured in any desired amount.

The procedure for using this embodiment to dispense floss 40 is the same as described for FIG. 5. To dispense liquid in any desired amount the user need only tip container 2.

FIG. 7 shows the embodiment of cork 12 which can be used in place of cork 11, FIG. 5 or cork 10 FIG. 6. This embodiment would be used to dispense floss 40 only. The procedure for dispensing floss 40 in this embodiment would be to pull out the desired length of floss 41, tuck it under cut off device 50 and pull.

FIG. 8 shows one preferred position of cut off device 50 on the elongated neck 2B of container 2.

FIG. 9 shows an alternative position of cut off device 50 on the body of container 2.

FIG. 10 Shows a roll of floss 40 wound on a mandrel 80. The mandrel in turn is placed over tube 30. This permits manufacturing of floss rolls 40 at one location for assembly to tube 30 at another location should that prove most economical. Also shown is Floss guide 42 which can make the pulling of floss 41 easier by guiding the floss around the curved shape of the guide 42 rather than having the floss string 41 take a sharp turn up the bare end of tube 30.

FIG. 11 Shows a floss roll 30 wound directly onto the outside surface of tube 30.

CONCLUSIONS AND RAMIFICATIONS

Examination of prior art shows that literally thousands of persons skilled in the dental arts have utilized dental floss in its dry state. Thousands of others have used dental floss which has been impregnated with flavoring or medication and then dried and packaged. Others have used brushes or other devices to coat or seal the teeth. No one has combined the ability to dispense both oral rinses and wet dental floss from a single container until this invention.

Many patents have been issued which allow the dispensing of wet dental floss. None of these inventions seem to have been able to penetrate the market, at least Applicant has not been able to find a single item of this description for sale anywhere at any price. The reasons for this are apparent when the individual inventions are examined. Cost is the principle factor. Cost of tooling, cost of manufacture and cost of gaining consumer acceptance.

Applicants invention does not have these problems since the cost of applicant's invention is lower than the separate costs of purchasing the two individual products necessary to accomplish the same results. Current advertising and marketing channels could be utilized to sell the concept. The manufacturer would be able to increase his sales with little, if any, additional marketing expense.

The added convenience and improved performance in preventing cavities for less cost is a synergistic result of this invention. It is certainly desirable to improve the dental health of the American people. From a cost and convenience aspect, Applicant's invention stands a good chance of accomplishing this objective.

What I claim is:

1. A floss dispensing device comprising:
   a. a container for housing a fluid, said container having an opening
   b. a closure supported by said container, said closure having an aperture therethrough
   c. a tube attached to said closure and extending downward from said closure to the approximate bottom of said container
   d. a quantity of floss suspended in said container
   e. a string of floss from said quantity of floss extending upwardly through said tube and out of said aperture of said closure to allow said string of floss to be grasped by the user and extended to a desired length, whereby said string of floss is capable of being wetted by said fluid of said container while being withdrawn from said container.

2. The floss dispensing device of claim 1, further comprising a closure lid for removably sealing said aperture of said container.

3. The floss dispensing device of claim 2, further comprising a floss cutting device attached to said closure lid.

4. The floss dispensing device of claim 2, further comprising a floss cutting device attached to said container.

5. The floss dispensing device of claim 1, wherein said closure of said container includes a plurality of dispensing openings therethrough and said floss dispensing device further comprises a closure lid attached thereto for removably sealing both said dispensing openings and said aperture in said closure of said container.

* * * * *